(12) United States Patent
DeMarais et al.

(10) Patent No.: US 6,355,057 B1
(45) Date of Patent: Mar. 12, 2002

(54) STAGGERED ENDOLUMINAL STENT

(75) Inventors: Denise M. DeMarais, San Jose; Darin C. Gittings, Sunnyvale, both of CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/287,143

(22) Filed: Apr. 6, 1999

Related U.S. Application Data

(63) Continuation-in-part of application No. 09/231,939, filed on Jan. 14, 1999, now abandoned.

(51) Int. Cl.[7] .................................................. A61F 2/06
(52) U.S. Cl. .................................................... 623/1.15
(58) Field of Search .............................. 623/1.11, 1.13, 623/1.15, 1.17, 23.7

(56) References Cited

U.S. PATENT DOCUMENTS

| | | | |
|---|---|---|---|
| 5,354,308 A | * | 10/1994 | Simon et al. ............... 623/1.15 |
| 5,411,552 A | * | 5/1995 | Andersen et al. .......... 623/2.22 |
| 5,514,154 A | | 5/1996 | Lau et al. |
| 5,575,816 A | | 11/1996 | Rudnick et al. |
| 5,676,696 A | | 10/1997 | Marcade |
| 5,697,971 A | | 12/1997 | Fischell et al. |
| 5,716,365 A | | 2/1998 | Goicoechea et al. |
| 5,716,393 A | | 2/1998 | Lindenberg et al. |
| 5,725,572 A | | 3/1998 | Lam et al. |
| 5,766,237 A | | 6/1998 | Cragg |
| 5,824,042 A | * | 10/1998 | Lombardi et al. ......... 623/1.15 |
| 5,824,059 A | | 10/1998 | Wijay |
| 5,827,321 A | | 10/1998 | Roubin et al. |
| 5,836,964 A | | 11/1998 | Richter et al. |
| 5,843,175 A | | 12/1998 | Frantzen |
| 5,897,589 A | * | 4/1999 | Cottenceau et al. ....... 623/1.15 |
| 6,027,526 A | * | 2/2000 | Limon et al. ............... 623/1.15 |
| 6,053,941 A | * | 4/2000 | Lindernberg et al. ...... 623/1.15 |
| 6,056,775 A | | 5/2000 | Borghi et al. |
| 6,123,722 A | * | 9/2000 | Fogarty et al. ............. 623/1.11 |
| 6,132,461 A | * | 10/2000 | Thompson .................. 623/1.15 |
| 6,162,245 A | * | 12/2000 | Jayaraman .................. 623/1.15 |
| 6,174,328 B1 | * | 1/2001 | Cragg ......................... 623/1.16 |

FOREIGN PATENT DOCUMENTS

| | | |
|---|---|---|
| EP | 0 832 618 | 4/1998 |
| WO | WO 97/27959 | 8/1997 |
| WO | WO 97/37617 | 10/1997 |
| WO | WO 99/12495 | 3/1999 |

* cited by examiner

*Primary Examiner*—David H. Willse
*Assistant Examiner*—Suzette J. Jackson
(74) *Attorney, Agent, or Firm*—Stern, Kessler, Goldstein & Fox P.L.L.C.

(57) ABSTRACT

Endoluminal prostheses, prosthetic systems, and methods for preparation and use of endoluminal prostheses for treatment of diseased body lumens make use of endoluminal prosthetic frame structures having circumferentially interspersed large and small expansible elements. These expansible elements, which are typically diamond-shaped, will generally decrease in length as the tubular frame expands radially. The prosthesis will often include a tubular liner supported by an axial series of ring frames having alternating large and small diamond elements, and can be loaded in a delivery catheter with the axial apices of the large diamond-shaped elements aligned with a small diamond-shaped element of an adjacent frame ring. To maintain adequate column strength, the adjacent ring frames may be attached to the liner so that the ring frames rotate relative to each other during expansion. The large diamond-shaped elements of adjacent ring frames can be aligned together once the prosthesis is expanded in the body lumen to enhance column strength.

19 Claims, 8 Drawing Sheets

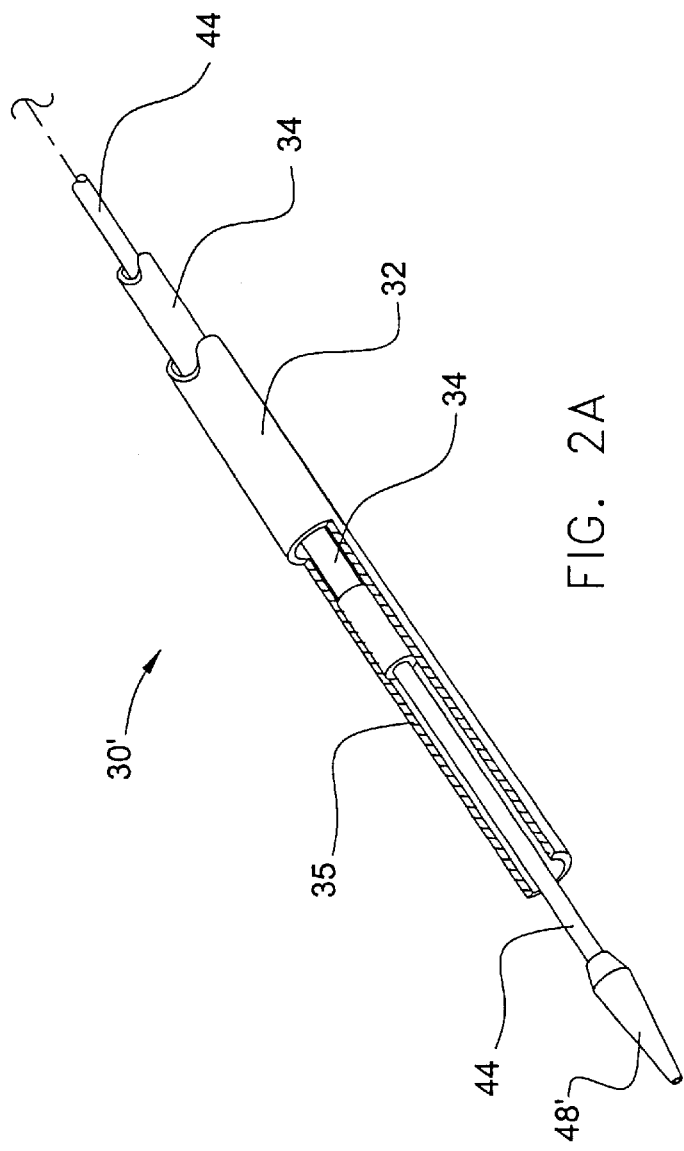
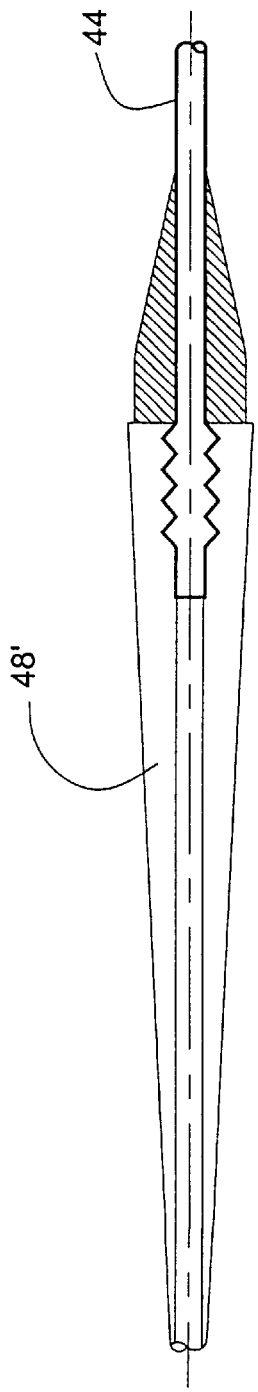
FIG. 2A
FIG. 2B

STAGGERED ENDOLUMINAL STENT

CROSS-REFERENCE TO RELATED APPLICATIONS

This application is a continuation-in-part of, and claims the benefit of priority from, co-pending U.S. patent application Ser. No. 09/231,939, filed Jan. 14, 1999, abandoned the full disclosure of which is incorporated herein by reference.

BACKGROUND OF THE INVENTION

1. Field of the Invention

The present invention relates generally to stents, stent-grafts, and other endoluminal prostheses for use in blood vessels and other body lumens. In particular, the present invention provides an endoluminal prosthesis frame which is highly compressible for deployment from a small delivery catheter, and which provides enhanced structural support when expanded in the body lumen.

The use of stents and other endoluminal prostheses is often indicated when there is a desire to maintain patency of a body lumen. Stents have commonly been used in blood vessels, the ureter, and the biliary duct to treat luminal obstructions and/or weakness. Of particular interest to the present invention, vascular stents have demonstrated significant success in inhibiting restenosis following angioplasty and other primary interventional treatments in the vasculature. Lined stents, often referred to as vascular stent-grafts, hold great promise for the reinforcement of blood vessels for the treatment of aneurysms, for lining blood vessels for the treatment of occlusive disease, and other conditions. In the case of aneurysms, the stent acts as a scaffold or framework for supporting a liner within the blood vessel to define an artificial blood vessel lumen. In the case of occlusive disease, the stent maintains luminal patency while the liner inhibits cellular intrusion into the lumen.

Vascular stents are typically delivered in a radially reduced or constrained configuration, and are expanded in situ at the target site. The stents may be plastically deformable and mechanically expanded at the target site, typically using a balloon catheter. Alternatively, the stents may be formed from a resilient material and released to self-expand at the target site. In a third general approach, the stents are formed from a shape-memory alloy and induced to expand at the target site by exposure to a temperature change. Regardless, the stent will usually comprise a network or lattice of structural elements which accommodates radial expansion from a small profile configuration (suitable for introduction and positioning of the prosthesis within the blood vessel), to a large profile configuration (in which the tubular prosthesis engages and supports the surrounding vascular wall). One common geometry for these stent frames comprises a plurality of diamond-shaped elements which are joined in a ring. These diamond-shaped elements are circumferentially expandable as the prosthesis is deployed from the small profile configuration to the large profile configuration. Other common geometries include helically wound wires and filaments, zig-zag rings, braided filaments, woven helical filaments and the like.

One disadvantageous characteristic that many prosthetic frame structures have in common is an axial length/diameter coupling effect: the axial length of at least some of the frame elements tends to decrease as the frame expands radially during deployment. With some frame structures, this coupling can lead to challenges in selecting the proper prosthesis size, and in positioning of the prosthesis during deployment. Fortunately, the overall axial variability of other frame structures is significantly less (so as to allow accurate positioning of the ends) while deployment of endoluminal prostheses for many applications does not require that the exact overall prosthetic length be known prior to deployment. These endoluminal therapies are gaining acceptance for use in treatment of diseased body lumens.

To still further enhance the efficacy of these endoluminal therapies and reduce the trauma to the patient, it is generally desirable to minimize the size (and specifically the cross-sectional dimensions) of the delivery system and prosthesis prior to deployment. For the prosthesis to effectively treat a diseased body lumen, it should have sufficient structural integrity and strength. These factors are generally enhanced by increasing the size of the structural elements of the expandable frame or stent. The structural design challenges can be particularly problematic when the frame comprises a resilient structure which is tightly compressed within a deployment catheter. The competing factors often dictate that a larger than ideal delivery system be used for many endoluminal therapies, which may make accessing the diseased region difficult, traumatic, and/or impossible.

In light of the above, it would generally be desirable to provide improved endoluminal prosthetic structures, methods, and delivery systems. In particular, it would be beneficial to provide improved prosthetic frames having the desired structural strength and integrity, but with a reduced overall delivery system profile. It would be best if these improvements could be provided using existing stent production in prosthetic assembly in deployment techniques to further enhance the applicability of these therapies.

2. Description of the Background Art

Exemplary methods for making stents are described in published PCT Application WO 97/27959, having a priority date of Jan. 30, 1996, and European Patent Application No. 97906450.8, filed Jan. 29, 1997, the full disclosures of which are incorporated herein by reference. An exemplary delivery device for endoluminal prostheses is described in Provisional U.S. Application Serial No. 60/102,562, filed on Sep. 30, 1998, the full disclosure of which is also incorporated herein by reference.

U.S. Pat. No. 5,676,696 describes modular bifurcated intraluminal grafts and methods for their delivery and assembly. U.S. Pat. No. 5,716,365 describes a bifurcated endoluminal prosthesis, while U.S. Pat. No. 5,716,393 describes a stent with an end of greater diameter than its body. U.S. Pat. No. 5,766,237 describes a method for reinforcing a body vessel using an intraluminal stent.

SUMMARY OF THE INVENTION

Present invention provides improved endoluminal prostheses, prosthetic systems, and methods for preparation and use of endoluminal prostheses for treatment of diseased body lumens. The invention generally provides endoluminal prosthetic frame structures having circumferentially interspersed large and small expansible elements. These expansible elements, which are typically diamond-shaped, will often decrease in length as the tubular frame expands radially, although the overall length of the prosthetic frame and prosthesis will remain substantially constant. The prosthesis will often include a tubular liner supported by an axial series of ring frames having alternating large and small diamond elements, and can be loaded in a delivery catheter with the axial apices of the large diamond-shaped elements aligned with a small diamond-shaped element of an adjacent frame ring. To maintain adequate column strength, the adjacent ring frames may be attached to the liner so that the ring frames rotate relative to each other during expansion. As a result, the large diamond-shaped elements of adjacent ring frames can be aligned together once the prosthesis is expanded in the body lumen. This enhances the structural integrity of the prosthesis, particularly the expanded prosthetic column strength.

Work in connection with the present invention has shown that the frames of resilient endoluminal prostheses often become jumbled, overlapping in a disordered manner when tightly compressed in a small delivery catheter. For example, as independent ring frames of diamond-shaped elements are compressed radially, the apices extending axially toward adjacent ring frames increase in length. As the apices of adjacent ring frames will preferably be in close proximity and/or in contact once the prosthesis is expanded in the body lumen (so as to provide adequate column strength) the enhanced axial length of the apices in the small profile configuration results in these structures interfering and/or overlapping radially when compressed. To overcome this disadvantageous interference, the present invention accommodates the increased axial length of these apices using interspersed and often circumferentially alternating diamond-shaped expansion elements. While these smaller elements do help the frame both expand radially and support the liner, they do not generally contact the apices of adjacent ring frames when expanded. These smaller elements act as spacers when the ring frames are radially compressed to help ensure that the apices of adjacent ring frames have room to expand axially without overlapping during compression.

In a first aspect, the present invention provides an endoluminal prosthesis comprising a tubular frame having a proximal end, a distal end, and an axis therebetween. The frame is radially expansible from a small diameter configuration to a large diameter configuration for deployment within a body lumen. The frame comprises a circumferentially oriented frame loop defining a plurality of short, axially-oriented apices. The frame further comprises a plurality of long, axially-oriented apices which extend axially beyond the short apices. The long apices are circumferentially interspersed with the short apices.

In another aspect, the invention provides an endoluminal prosthesis comprising a first frame loop defining axial and circumferential orientations. The first frame loop includes interspersed large and small expandable elements. The large elements are axially longer than the small elements. A second frame loop is aligned co-axially with the first frame loop. The second frame loop is circumferentially expandable and includes interspersed large and small expandable elements. The large expandable elements are larger than the small expandable elements. At least one of the large expandable elements of the first frame loop is axially aligned with one or more associated small expandable elements of the second frame loop when the first and second frame loops are in a small profile configuration. At least one of the large expandable elements of the first frame loop is axially aligned with an associated large expandable element of the second frame loop when the first and second frame loops are in a large profile configuration.

In yet another aspect, the invention provides a tubular prosthesis for deployment within a blood vessel. The prosthesis comprises a tubular liner defining axial and circumferential orientations. A first ring frame supports the liner, and has an axial end. The first ring frame includes interspersed large and small diamond-shaped elements, the large elements defining apices adjacent the end. A second ring frame supports the liner adjacent the axial end of the first ring frame. The second ring frame includes interspersed large and small diamond-shaped elements. The apices of the first ring frame are disposed circumferentially between the large diamond-shaped elements of the second ring frame when the prosthesis is in a small profile configuration for insertion into the blood vessel. The apices of the first ring frame are axially aligned with the large diamond-shaped elements of the second ring frame when the first and second ring frames are in a large profile configuration engaging the surrounding blood vessel. The first and second ring frames rotate axially relative to each other as the prosthesis expands.

In yet another aspect, the invention provides a method for preparing an endoluminal prosthesis for deployment. The method comprises affixing a first ring frame to a tubular liner. The first ring frame has circumferentially interspersed small and large expandable elements. The second ring frame is affixed to the tubular liner and axially adjacent the first ring frame, the second ring frame also having circumferentially interspersed small and large expandable elements. The prosthesis is loaded into a delivery catheter in a small configuration with the large expandable elements of the first ring frame circumferentially interspersed with the large expandable elements of the second ring frame.

BRIEF DESCRIPTION OF THE DRAWINGS

FIGS. 2A and B illustrate an alternative delivery system for deploying the prosthesis of FIG. 1.

DESCRIPTION OF THE SPECIFIC EMBODIMENTS

Figure 1:
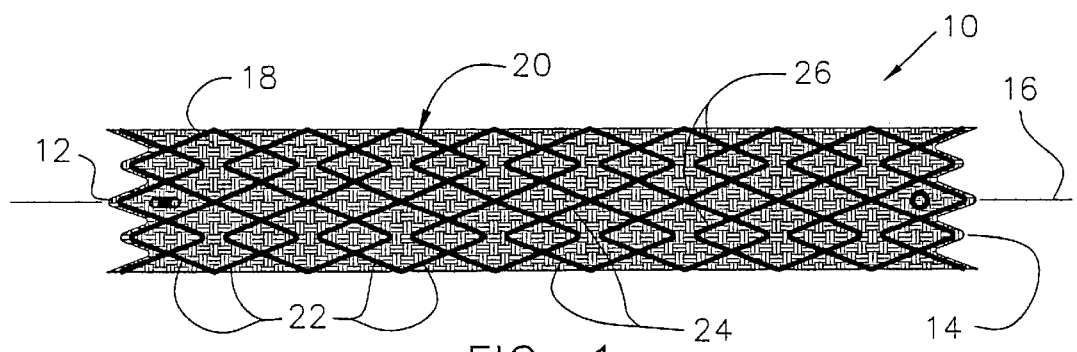
FIG. 1 is a side view of an endoluminal prosthesis according to the principles of the present invention.

Referring now to FIG. 1, an endoluminal stent-graft 10 generally comprises a tubular structure having a proximal end 12, a distal end 14, and an axis 16 therebetween. Stent-graft 10 includes a liner 18 supported by a frame 20, the frame here defined by an axial series of independent ring frames 22 affixed to inner liner 18. Each of ring frames 22 is formed as a circumferential series of alternating large diamond-shaped elements 24 and small diamond-shaped elements 26. In the embodiment illustrated in FIG. 1, frame 20 is disposed outside of a tubular liner 18 so as to provide a smooth prosthetic lumen. Optionally, a surface of the liner may be disposed over the ring frames, either instead of inner liner 18 or in combination therewith.

To secure ring frames 22 to liner 18, the liner is typically sutured to the frame. A wide variety of alternative liner/frame attachment mechanisms are available, including adhesive bonding, heat welding, ultrasonic welding, weaving or braiding the frame elements into the liner, and the like.

Prosthesis 10 will typically have a length in a range from about 20 mm to about 500 mm, the length preferably being in a range from about 50 mm to about 200 mm, the length of the single lumen stent-graft illustrated ideally being in range from about 59 mm to about 120 mm. A relaxed diameter of prosthesis 10 will generally be in a range from about 7 mm to about 44 mm, the diameters ideally being in range from about 12 mm to about 32 mm. The number of ring frames 22 used to support liner 18 of prosthesis 10 will vary with both the length and diameter of the prosthesis, the number of ring frames typically being in a range from about 4 to about 25, and ideally being in a range from about 5 to about 12. These sizes and ranges are particularly suitable for treatment of aneurysms, including aortic aneurysms.

While the invention can be clearly understood with reference to the straight tubular prosthesis 10 of FIG. 1, it should be understood that the staggered ring frame of the present invention will also provide advantages for more complex prosthetic systems, including bifurcated prostheses, prosthetic systems having multiple modules for assembly in situ, and the like. Similarly, while these structures will generally be described with reference to prosthetic frames having circumferentially continuous ring frames, it should be understood that the inventions also encompasses frames formed with helical or wound expansible elements. As used herein, the term "loop" encompasses both ring frames and the windings of such helical frames.

Liner 18 will typically comprise a flexible polymer membrane. Suitable liners may be formed as a continuous woven tube of a polyester such as Dacron™, or the like. Liners may alternatively be formed from braided polyester or other fibers, from a porous polytetrafluorethylene such as Teflon™, or other biocompatible materials. Liner 18 may be substantially inexpansible, or may alternatively expand either resiliently or plastically. Liner 18 will preferably comprise a sufficiently porous material to accommodate cellular in-growth, but will not have pores of a sufficient size to allow the cells to proliferate into and occlude the lumen of the prosthesis.

While frame 20 will generally be resilient, the present invention will also have advantages when used with plastically deformable prosthetic structures. Suitable biocompatible deformable structures may be formed from a wide variety of metals or polymers, typically comprising platinum, stainless steel, or the like. For such plastically deformable structures, the invention will enhance the structural integrity and strength of the expanded prosthetic frame which can be delivered with a delivery system having a given cross-section. Stated differently, the invention will allow the use of smaller prosthetic devices and delivery systems providing a desired structural strength. Nonetheless, the present invention will find its most immediate applications with resiliently expansible prostheses, as it will generally allow the compression of these prostheses into smaller in diameter delivery catheters. These smaller delivery systems will often have greater axial flexibility than known delivery catheters, and by avoiding radial overlap between adjacent ring frames, the axial flexibility of the prosthesis within the delivery system is also improved.

Figure 2:
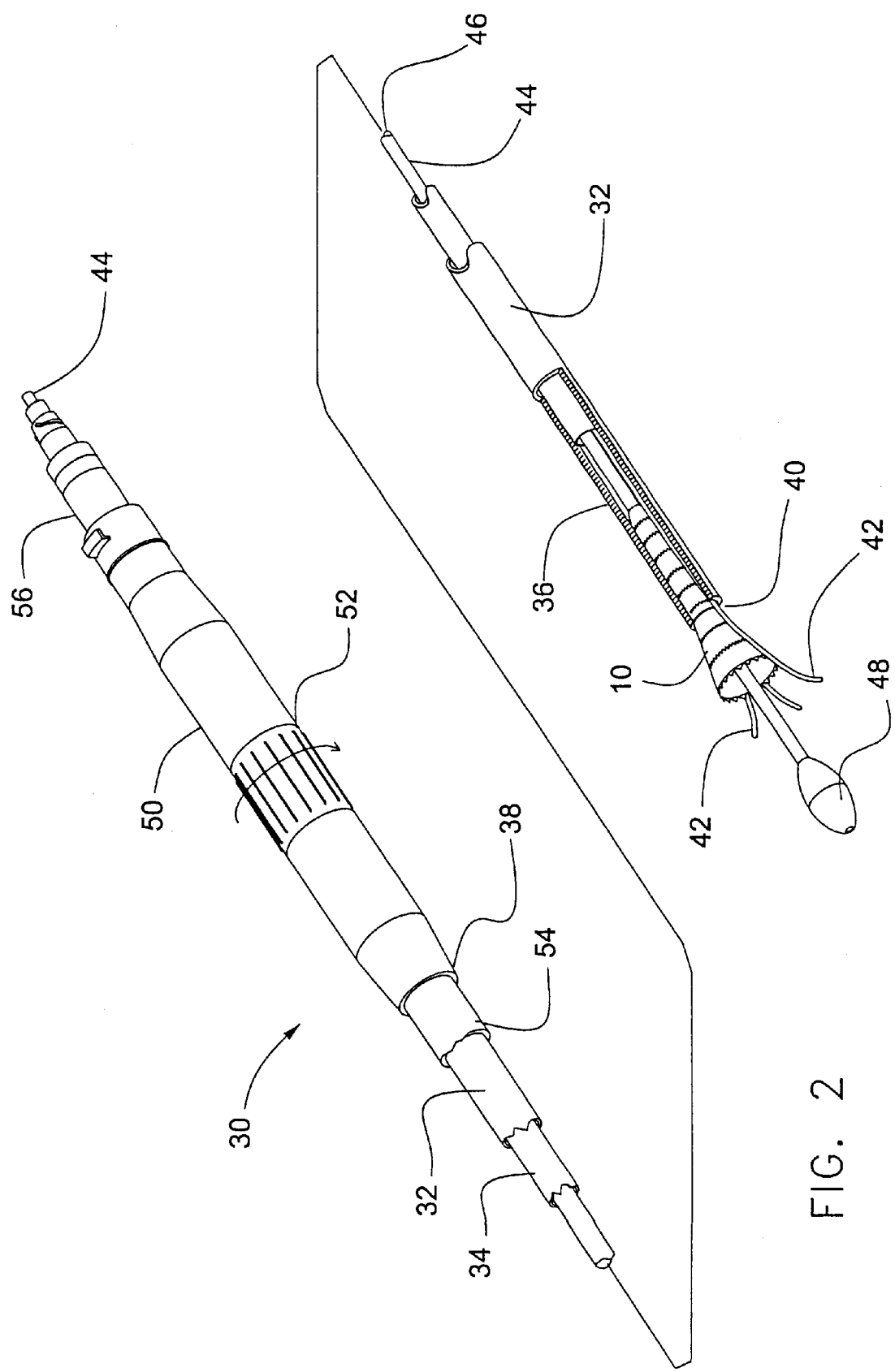
FIG. 2 is a delivery system for deployment of the prosthesis of FIG. 1.

Referring now to FIG. 2, an exemplary delivery system 30 comprises a tubular sheath 32 and a shaft 34. Sheath 32 has a lumen 36 extending from a proximal end 38 to a distal end 40. Shaft 34 is slidably received within lumen 36, and a plurality of runners 42 extend distally from the shaft. Runners 42 line a portion of the inner surface of lumen 36, and slide within the lumen of the shaft. Shaft 34 also has a lumen, in which a coreshaft 44 is affixed so as to provide a guidewire lumen 46. Nose cone 48 is affixed to the distal end of coreshaft 44.

Prosthesis 10 is radially compressed and restrained within runners 42. In turn, sheath 32 prevents runners 42 from expanding outwardly. Runners 42 are formed from a hard material and distribute the expansile load from the frame of prosthesis 10 over the inner surface of lumen 36. The housing 50 at the proximal end 38 of sheath 32 contains an actuation mechanism for withdrawing sheath 32 proximally while prosthesis 10 remains axially restrained by runners 42. More specifically, to withdraw sheath 32 proximally, a handle 52 is rotated about the axis of the sheath, as illustrated.

An outer tube 54 extends from housing 50, while shaft 34 extends through housing 50 and is affixed to a connector 56. Connector 56 releasably attaches shaft 34 to the proximal end of housing 50, so that shaft 34 and outer tube 54 can be affixed relative to each other while sheath 32 is withdrawn to deploy the prosthesis. Hence, the delivery system can be stabilized using outer tube 54, for example, by inserting the outer tube into a sealing member of an introducer valve. The use and structure of delivery system 50 is more fully described in U.S. Pat. No. 6,203,550, the full disclosure of which is incorporated herein by reference.

A distal portion of an alternative delivery system 30' is illustrated in FIGS. 2A and B. Beginning at the distal end, nosecone 48' here comprises a polymer such as Pebax™, Hytrel™, or the like, and is preferably injection molded. The contrast of nosecone 48' under fluoroscopy can be enhanced by including a high contrast material such as between about 10 and 40% barium sulfate, depending on the size of the nosecone.

Coreshaft 44 may comprise a polymer such as a polyimide. Attachment of the coreshaft and nosecone is preferably provided by buckling a distal portion of the coreshaft and overmolding the nosecone onto the buckled portion, as illustrated in FIG. 2B.

Rather than holding the prosthesis within runners, a piston 35 engages a proximal end of the prosthesis to hold the prosthesis while sheath 32 is withdrawn proximally. Piston 35 may comprise a high strength radiopaque material such as a stainless steel, and may be fittingly received within the lumen of the sheath 32. Piston 35 can be heated to melt and affix shaft 34 to the piston where the shaft comprises PEEK. Sheath 32 preferably also comprises PEEK, and should be 13 Fr or smaller for deployment of an iliac prosthetic module.

Figures 3A, 3B, 3C:
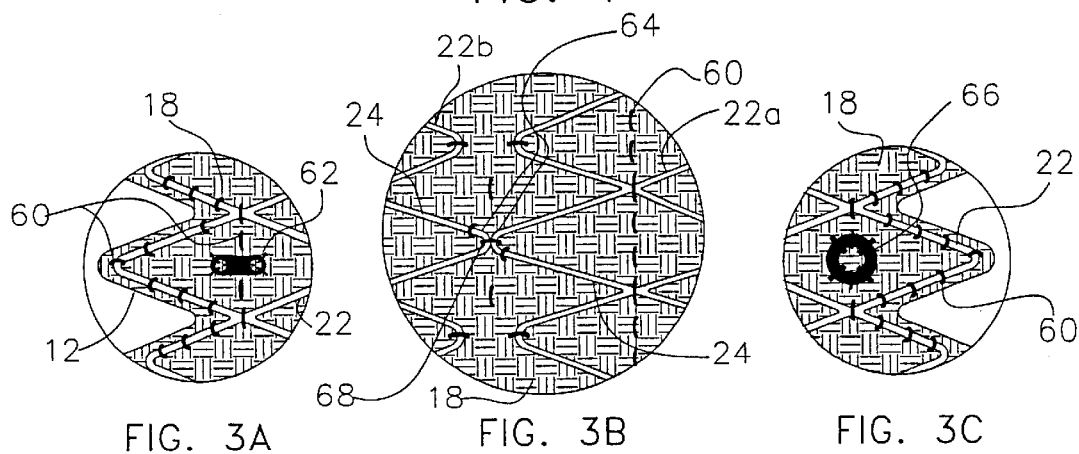
FIGS. 3A through 3C are detailed views illustrating the construction of the prosthesis of FIG. 1.

Referring now to FIG. 3A, sutures 60 affix liner 18 along proximal end 12 as defined by ring frame 22 so as to substantially seal the liner of the prosthesis against the surrounding vascular wall. Sutures 60 also affix position indicating markers 62, as more fully described in published PCT Pat. Application No. WO 97/37616, the full disclosure of which is incorporated herein by reference. Sutures 60 affix the frame and marker structures to the adjacent liner.

Referring now to FIG. 3B, large diamond-shaped elements 24 of adjacent first and second ring frames 22a, 22b are in axial alignment when the prosthesis is in the large profile configuration. More specifically, apices 64 defined by large diamond-shaped elements 24 are held in close proximity by stitching 60. Stitching 60 will typically comprise a suture material such as polyester, but may alternatively comprise a wide variety of biocompatible polymers. In some embodiments, stitching 60 may be replaced by alternative mechanisms for attachment of ring frames 22 to liner 18, as described hereinabove.

FIG. 3C illustrates liner 18, ring frame 22, and stitching 60 adjacent distal end 14, and also shows the optional use of an alternative radiopaque marker 66 which can help to differentiate the ends of the prosthesis when viewing the prosthesis under a fluoroscope, ultrasound, or some other medical imaging modality. Alternatively, similar markers may be used at both ends. A slightly enhanced separation between a ring frame at the end of the prosthesis (preferably the last-compressed end when the prosthesis is loaded into the delivery system) and the adjacent ring frames accommodates some axial displacement of the ring frames during compression and/or deployment.

Figures 4A, 4B:
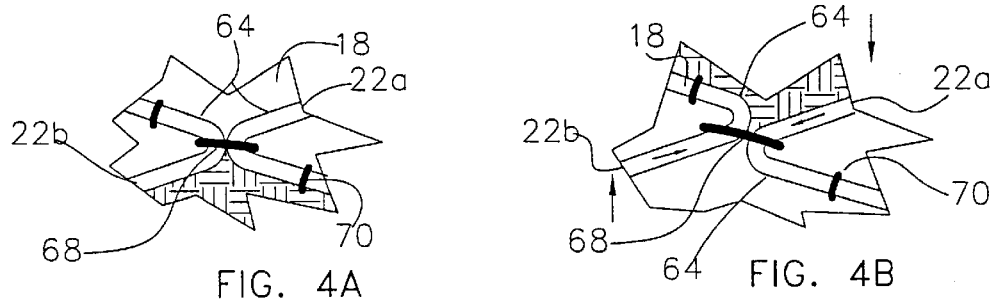
FIGS. 4A through C schematically illustrate the interaction between adjacent ring frames during compression or expansion of the prosthesis of FIG. 1.
Figure 4C:
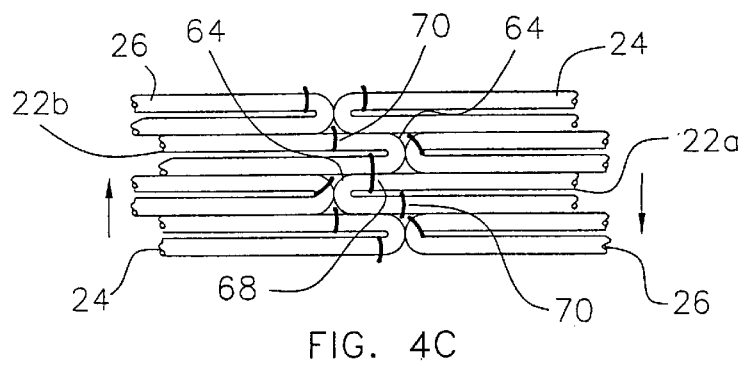

The structure and use of the specific stitches used to attach ring frames 22 to liner 18 adjacent apices 64 can be understood with reference to FIGS. 4A through C. A connector stitch 68 extends over structural elements of first and second ring frames 22a, 22b adjacent apices 64 when the prosthesis is in the large profile configuration, as can be seen in FIGS. 3B and 4A. Associated slider loops 70 extend over the lower and upper arms of first and second ring frames 22a, 22b at a point on liner 18 separated from apices 64.

As can be understood with reference to FIGS. 4B and C, each apex 64 extends farther from the center line of the associated ring frame 22 when prosthesis 10 is radially compressed. This elongation of the diamond-shaped elements is caused by the reorientation of the structural elements of the "diamonds:" the four frame elements defining each diamond are more and more aligned with the axis of the prosthesis when the prosthesis is compressed, rather than angling axially and circumferentially. As a result, apices 64 advance axially towards each other. At the same time, the structural arms defining each apex move radially towards each other. As first ring frame 22a is attached to liner 18 by slider stitch 70 along its lower arm, and as second ring frame 22b is attached to liner 18 by a slider loop over its upper arm, the first ring frame will tend to rotate downward relative to the second ring frame as prosthesis 10 compresses. This relative rotation may be further encouraged by the sliding of the apices against each other as they advance axially. Regardless, apices 64 of large diamond-shaped elements 24 conveniently extend axially between the large diamond-shaped elements of the adjacent ring frame, as illustrated in FIG. 4C. In this embodiment, the compressed large diamond-shaped elements 24 end up axially aligned with the compressed small diamond-shaped elements 26.

While the interaction of apices 64 of first and second ring frames 22a, 22b has been described with reference to compression of prosthesis 10, it should be understood that similar interactions effect relative rotation between the ring frames when the prosthesis expands. More specifically, a resilient prosthesis constrained in the small profile configuration illustrated in FIG. 4C (or a plastically expansible prosthesis prior to deployment) will experience a shortening of both large and small diamond-shaped elements 24, 26 when first and second ring frames 22a, 22b expand partially (as illustrated in FIG. 4B) toward a fully expanded configuration (as illustrated in FIGS. 4A and 3B). As large diamond-shaped elements 24 shorten, apices 64 slide along each other and into alignment under the constraint of connector stitch 68. Slider stitches 70 also urge the large diamond-shaped elements into axial alignment. Once aligned, the large diamond-shaped elements help improve column strength of prosthesis 10 by transmitting forces axially, either by direct engagement between apices 64, or by transmission of force through coupling stitch 68 and/or liner 18. It should be understood that only the apices of the large diamond-shaped elements will engage each other, so that the axial flexibility of the prosthetic frame will be greater than if all apices of adjacent ring frames were in engagement.

Figure 5A:
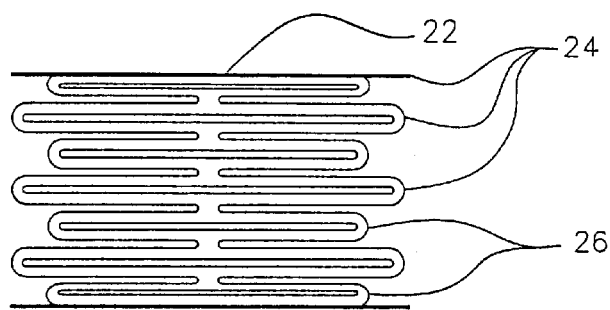
FIGS. 5A through C illustrate a single ring frame, a flat pattern of a ring frame, and a detail of the expanded diamond-shaped elements of a ring frame of the prosthesis of FIG. 1.
Figure 5B:
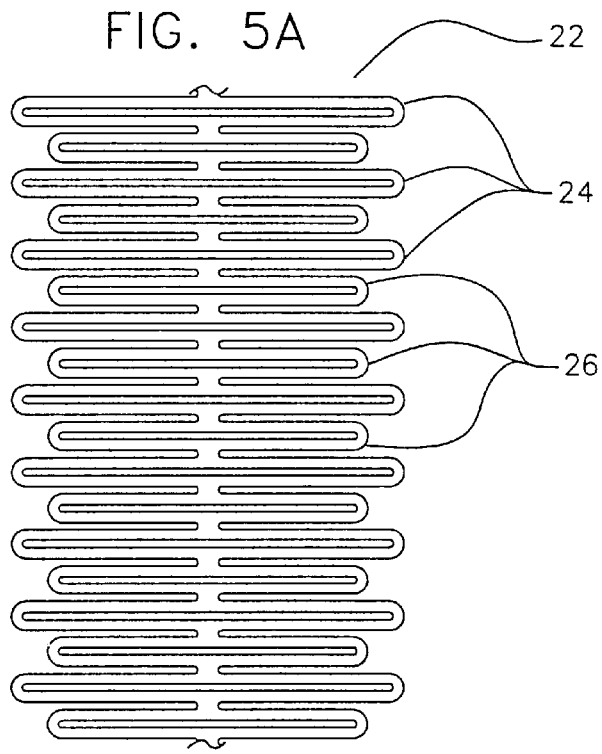
Figure 5C:
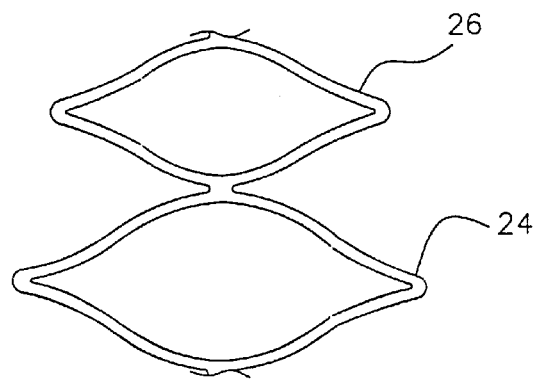

Frame 20 may comprise a variety of high strength, biocompatible metals or polymers. Frame 20 will preferably comprise a superelastic shape memory alloy such as Eligiloy™, Nitinol™, or the like. The structural elements forming large and small diamond-shaped elements 24, 26 may have a radial thickness of between about 0.008" and 0.020" the structural elements having a radial thickness in a range from about 0.013" to about 0.014" in the exemplary embodiments. The circumferential width of the structural elements along their lengths will typically be in a range from about 0.005" to about 0.015", the exemplary embodiments having structural elements with circumferential widths of between about 0.008" and 0.0115 " Ring frames 22 may optionally be formed by selectively cutting a cylindrical tube, as can be understood with reference to FIGS. 5A through C. FIG. 5A is a side view of ring frame 22 as formed in the small profile configuration. The ring frame may be formed by selectively removing the tube material so as to define the shape. Advantageously, such a ring frame has no welded or bonded joints which might fail after deployment. FIG. 5B illustrates a flat pattern view of the tubular structure illustrated in FIG. 5A.

When ring frame 22 comprises a plastically deformable material, it may be loaded on the deployment balloon (or other expansion device) for deployment. Once expanded, large and small diamond-shaped elements 24, 26 assume the shapes illustrated in FIG. 5C. Where ring frame 22 comprises a resilient material, it will often be expanded over a cylindrical mandrel and heat treated so that the ring frame is biased to return its expanded shape.

Figures 6A, 6B, 6C:
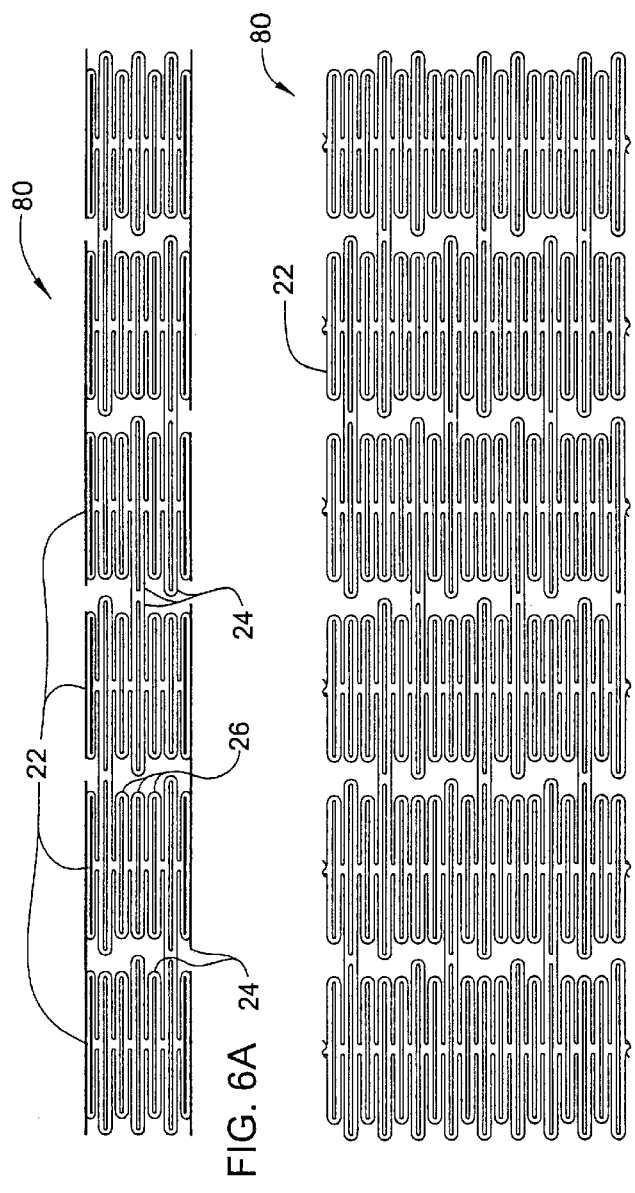
FIGS. 6A through C illustrate an axially continuous prosthetic frame having multiple interconnected ring frames in a side view, a flat pattern view, and an expanded detailed view.
Figure 7:
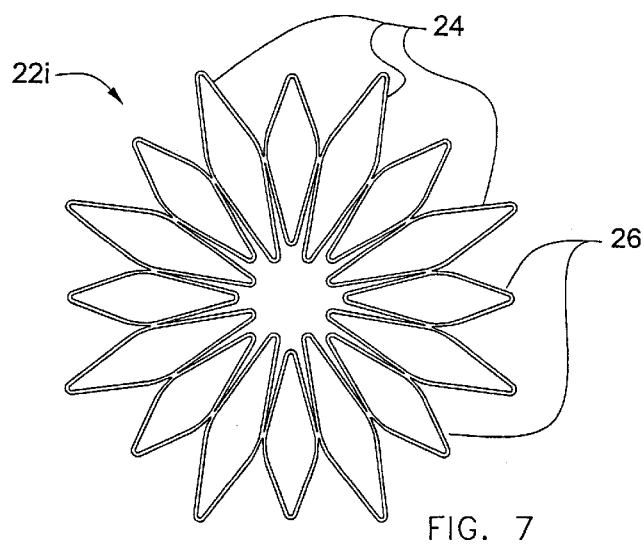
FIG. 7 illustrates a precursor for a ring frame of the prosthesis of FIG. 1 formed as a flat continuous series of diamond-shaped elements.
Figure 8A:
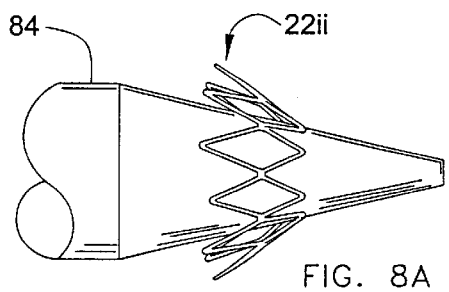
FIGS. 8A and B illustrate a method for everting the flat structure of FIG. 7 so as to produce a ring frame.
Figure 8B:
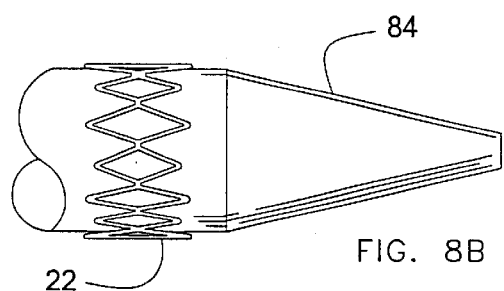

Referring now to FIGS. 6A through C, an axially continuous frame 80 includes an axial series of ring frames 22 having large diamond-shaped elements 24 interspersed with small diamond-shaped elements 26. However, in this embodiment, apices of selected large diamond-shaped elements 24 of adjacent ring frames are affixed together to define axial connector elements 82. As a result, there may be little or no relative rotation between adjacent ring frames during expansion or compression of axially continuous frame 80. Nonetheless, this structure can help prevent jumbling of the expansible elements when the prosthetic frame is compressed in a delivery sheath.

Alternative methods for fabricating ring frames 22 can be understood with reference to FIGS. 7 through 10B. Rather than cutting the ring frame from tubing, a precursor form of ring frame 22i comprises a substantially flat structure defining large and small diamond-shaped elements 24, 26 in a radial configuration reminiscent of a star or flower. Flat precursor 22i is everted over a mandrel 84 to an intermediate configuration 22ii, and then to a large profile configuration of ring frame 22 as shown in FIGS. 8A and B. The flat pattern ring frame is then set to the desired cylindrical shape by heat treatment while mounted on mandrel 84.

Figure 9:
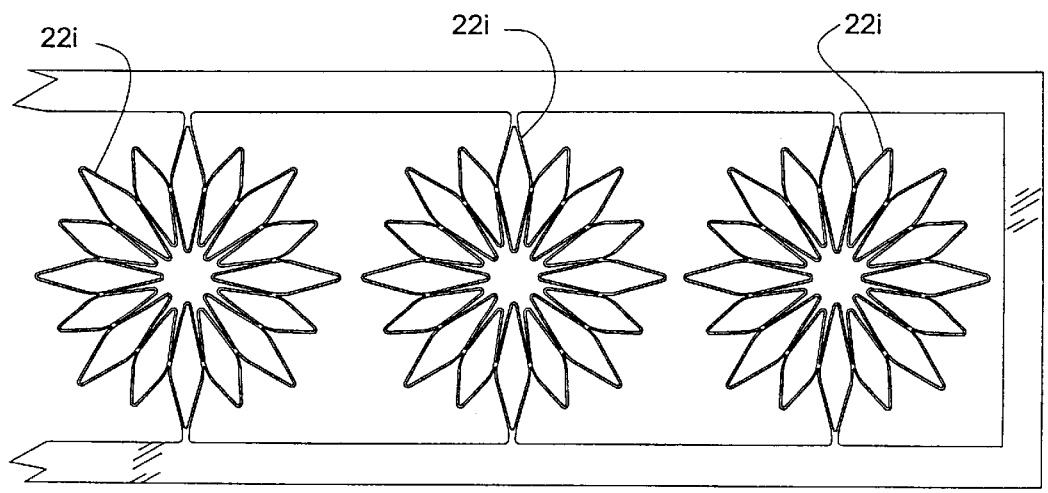
FIG. 9 illustrates a first method for fabricating the flat structure of FIG. 7.
Figure 10A:
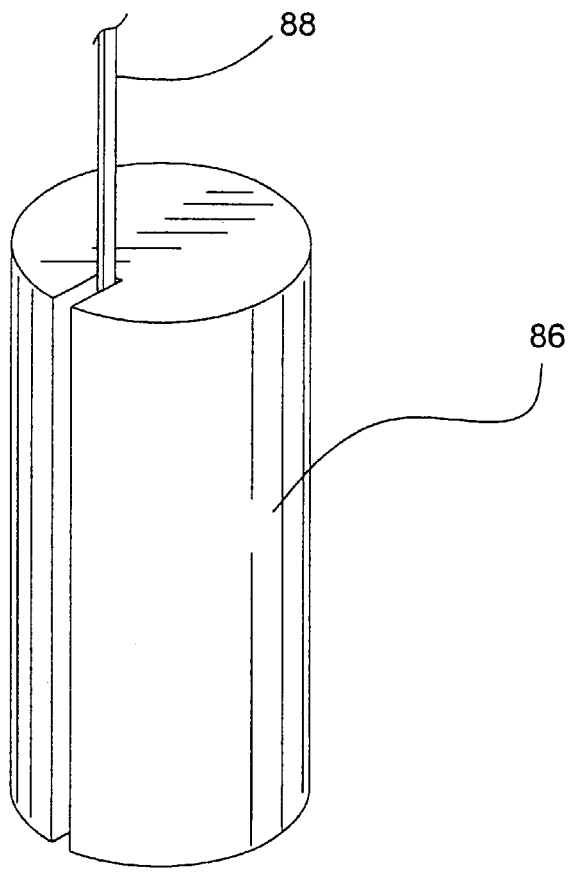
FIGS. 10A and B illustrate an alternative method for fabricating the flat structure of FIG. 7.
Figure 10B:
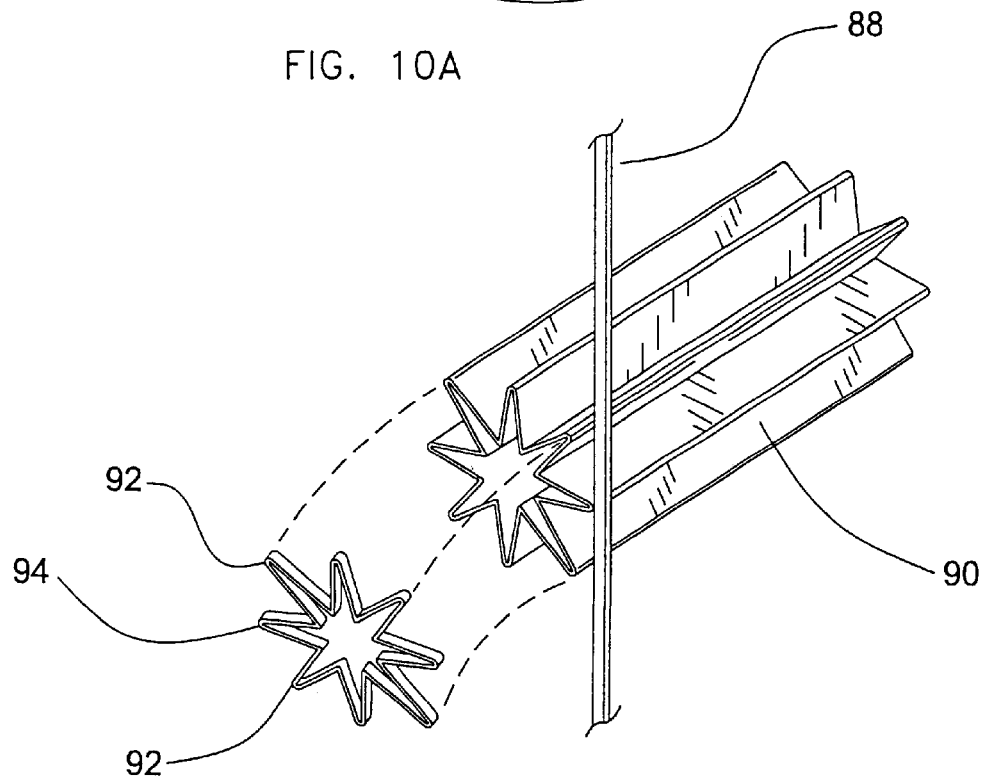

Advantageously, flat pattern ring frames may be mass produced as illustrated in FIGS. 9, 10A, and 10B. A plurality of flat pattern ring frame precursors 22i might be produced by stamping the precursors simultaneously from sheath stock, as can be understood with reference to FIG. 9. Alternatively, a rod stock 86 may be cut using, for example, an Electron Discharge Machining ("EDM") wire 88 to define star shaped tube 90. Tube 90 has a cross-section which may be substantially similar to the shape of ring frame precursor 22i (see FIG. 7), of the flat pattern, a zig-zag as shown in FIG. 10B, in a flat pattern sinusoid, or the like. Regardless, the expansible elements will preferably comprise interspersed large expansible elements 92 and small expansible elements 94, the large and small elements preferably alternating circumferentially. A large number of ring frame precursor flat patterns may then be formed by cutting cross-sectional slices from tube 90, as illustrated in FIG. 10B. These flat pattern ring frame precursors, having alternating large and small expansible elements, may then be everted as described above regarding FIGS. 8A and B so as to form final ring frame structures.

Figure 11:
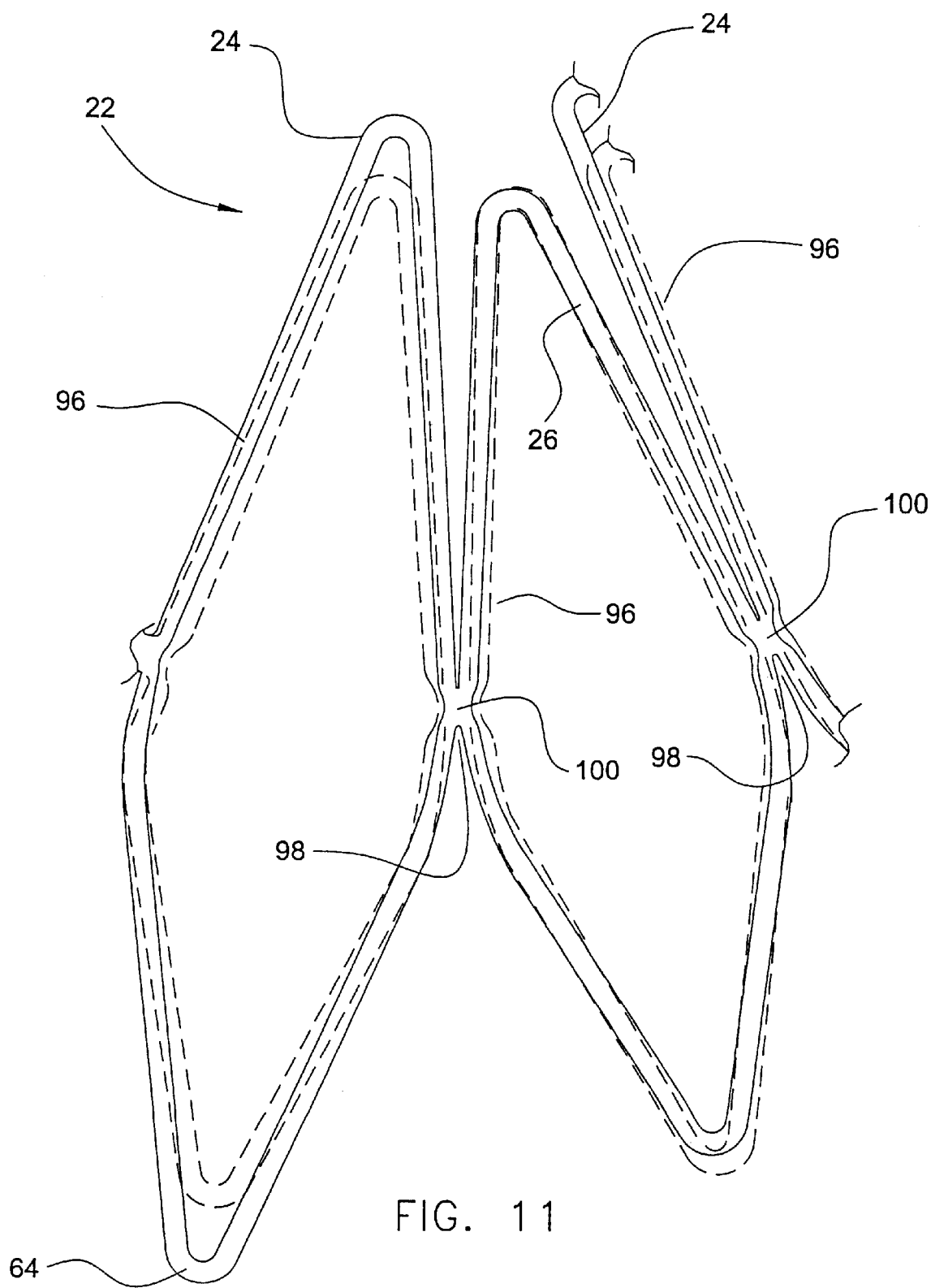
FIG. 11 schematically illustrates differences in the frame structure between the alternating large and small diamond-shaped elements to minimize the cross-section of the compressed prosthesis and a frame having uniform expandable elements.

Referring now to FIG. 11, a flat pattern ring frame having uniform diamond-shaped elements 96 is illustrated by dash lines for comparison to ring frame 22 having alternating large and small diamond-shaped elements 24, 26. Note that radial compressibility is enhanced through the use of reduced radii 98 and smaller circumferential inter-diamond connector 100 in ring frame 22.

While the invention has been described in some detail, for clarity of understanding and by way of example, a variety of changes, adaptations, and modifications will be obvious to those of skill in the art. Hence, the scope of the present invention is not limited to these specific examples, and is solely limited by the scope of the appended claims.

What is claimed is:

1. An endoluminal prosthesis comprising a tubular frame having a proximal end, a distal end, and an axis therebetween, the tubular frame being radially expansible from a small diameter configuration to a large diameter configuration for deployment within a body lumen, the tubular frame comprising a first circumferentially oriented frame loop and a second circumferentially oriented frame loop, the first and the second frame loops each defining a plurality of short, axially oriented apices and a plurality of long, axially oriented apices, the long apices extending axially beyond the short apices, the long apices alternatingly interspersed with the short apices.

2. The endoluminal prosthesis of claim 1, wherein the long apices of the first and the second frame loops are axially adjacent and axially aligned so as to enhance column strength of the tubular frame when the tubular frame is in the large diameter configuration.

3. The endoluminal prosthesis of claim 2, wherein the short apices of the first frame loop are aligned with the long apices of the second frame loop when the frame is in the small diameter configuration.

4. The endoluminal prosthesis of claim 3, wherein t he long apices are defined by intersections of long frame members, and wherein centerlines of the first and second frame loops are separated by a separation distance which is less than a combined length of the adjacent long frame members of the first and second frame loops when the frame is in the small configuration.

5. The endoluminal prosthesis of claim 4, wherein the long apices of the first frame loop are disposed circumferentially between the long frame members of the second frame loop when the frame is in the small configuration, the long apices decreasing in axial length when the frame expands radially to the large configuration.

6. The endoluminal prosthesis of claim 3, further comprising a tubular liner supported by the tubular frame.

7. The endoluminal prosthesis of claim 6, wherein the first and second frame loops rotate relative to each other when the frame expands from the small diameter configuration to the large diameter configuration.

8. The endoluminal prosthesis of claim 7, further comprising stitches fastening the tubular liner to the first and second frame loops, the stitches engaging the first and second frame loops so that the stitches help effect the rotation.

9. The endoluminal prosthesis of claim 1, wherein the first and the second frame loops comprise a circumferential series of diamond-shaped frame elements, the diamond-shaped elements having circumferentially alternating large and small sizes.

10. The endoluminal prosthesis of claim 1, wherein at least one long apex of the first frame loop is affixed to an associated long apex of the second frame loop, at least one long apex of the first frame loop being axially aligned with an associated short apex of the second frame loop and at least one short apex of the first frame loop is axially aligned with an associated long apex of the second frame loop.

11. The endoluminal prosthesis of claim 10, wherein the affixed long apices bend and the associated long and short apices do not interfere when the tubular frame flexes axially.

12. An endoluminal prosthesis comprising:
    a first frame loop defining axial and circumferential orientations, the first frame loop including interspersed large and small expandable elements, the large elements being axially longer than the small elements;
    a second frame loop aligned coaxially with the first frame loop, the second frame loop being circumferentially expandable and including interspersed large and small expandable elements, the large expandable elements being larger than the small expandable elements;
    wherein at least one of the large elements of the first frame loop is axially aligned with an associated small element of the second frame loop when the first and second frame loops are in a small profile configuration; and
    wherein at least one of the large elements of the first frame loop is axially aligned with an associated large element of the second frame loop when the first and second frame loops are in a large profile configuration.

13. The endoluminal prosthesis of claim 12, wherein the large expandable elements of the first frame loop extend axially to apices adjacent the second frame loop, and wherein the apices of the first frame loop are disposed circumferentially between the large elements of the second frame loop when the first and second frame loops are in the small profile configuration.

14. The endoluminal prosthesis of claim 13, wherein the apices of the first frame loop are axially aligned with apices of the large elements of the second frame loop when the first and second frame loops are in the large profile configuration.

15. The endoluminal prosthesis of claim 14, wherein the first and second frame loops are independently attached to a tubular liner so that the first and second frame loops rotate axially relative to each other as the prosthesis expands circumferentially.

16. The endoluminal prosthesis of claim 12, wherein axial lengths of the expandable elements decrease as the expandable elements expand circumferentially, and wherein a distance between a circumferential centerline of the first frame loop and a circumferential centerline of the second frame loop remains constant as the endoluminal prosthesis expands from the small profile configuration to the large profile configuration.

17. A tubular prosthesis for deployment within a blood vessel, the prosthesis comprising:

a tubular liner defining axial and circumferential orientations;

a first ring frame supporting the liner, the first ring frame having an axial end and including interspersed large and small diamond-shaped elements, the large elements defining apices adjacent the end and being axially longer than the small elements;

a second ring frame supporting the liner adjacent the axial end of the first ring frame, the second ring frame including interspersed large and small diamond-shaped elements, the large diamond-shaped elements being larger than the small diamond-shaped elements, the apices of the first ring frame being disposed circumferentially between the large diamond-shaped elements of the second ring frame when the prosthesis is in a small profile configuration for insertion into the blood vessel, the apices of the first ring frame being axially aligned with the large diamond-shaped elements of the second ring frame when the first and second ring frames are in a large profile configuration engaging the surrounding blood vessel, the first and second ring frames rotating axially relative to each other as the prosthesis expands.

18. A tubular prosthesis for deployment within a blood vessel, the prosthesis comprising:

a tubular liner defining axial and circumferential orientations;

a first ring frame supporting the liner, the first ring frame defining a centerline and having an axial end and including expandable elements, the expandable elements defining an axial length that decreases when the first ring frame expands from a small profile configuration to a large profile configuration; and a second ring frame supporting the liner adjacent the axial end of the first ring frame, the second ring frame defining a centerline and including expandable elements, the expandable elements defining an axial length that decreases when the second ring frame expands from a small profile configuration to a large profile configuration, a separation distance between the centerlines of the first and second ring frames remaining substantially constant when the ring frames expand, the expandable elements of the second ring frames rotating into alignment with the expandable elements of the second ring frame when the first and second ring frames expand so as to enhance axial column strength of the expanded prosthesis.

19. A method for preparing an endoluminal prosthesis for deployment, the method comprising:

affixing a first ring frame to a tubular liner, the first ring frame having circumferentially interspersed small expandable elements and large expandable elements;

affixing a second ring frame to the tubular liner axially adjacent the first ring frame so that the second ring frame has circumferentially interspersed small expandable elements and large expandable elements; and loading the prosthesis into a delivery catheter in a small configuration with the large expandable elements of the first ring frame circumferentially interspersed with the large expandable elements of the second ring frame.

* * * * *